United States Patent [19]

Blixt et al.

[11] 4,184,920

[45] * Jan. 22, 1980

[54] ENZYMATIC SUBSTRATE COMPOSITION ADSORBED ON A CARRIER

[75] Inventors: Kjell G. Blixt; Sven I. A. Törnmarck, both of Malmö; Rolf Juhlin, Åkers Styckebruk; Karl R. Salenstedt, Upplands Väsby; Mandayam Tiru, Järfälla, all of Sweden

[73] Assignee: Kommanditbolaget Kockums Chemical AB & Co., Malmö, Sweden

[ * ] Notice: The portion of the term of this patent subsequent to Aug. 23, 1994, has been disclaimed.

[21] Appl. No.: 830,957

[22] Filed: Sep. 6, 1977

Related U.S. Application Data

[63] Continuation of Ser. No. 783,509, Mar. 31, 1977, which is a continuation of Ser. No. 489,667, Jul. 18, 1974, Pat. No. 4,043,871, which is a continuation-in-part of Ser. No. 354,412, Apr. 25, 1973, abandoned.

[30] Foreign Application Priority Data

Apr. 18, 1974 [SE] Sweden ................................ 7405199

[51] Int. Cl.$^2$ ............................................ G01N 31/14

[52] U.S. Cl. ...................................... 435/19; 435/805
[58] Field of Search ................... 195/99, 63, 66 R, 68, 195/101, 116, 103.5 R; 426/231

[56] References Cited

U.S. PATENT DOCUMENTS

| | | | |
|---|---|---|---|
| 2,671,028 | 3/1954 | Clark | 195/103.5 R |
| 2,769,750 | 11/1956 | Harris | 195/116 |
| 2,971,850 | 2/1961 | Darton | 195/99 |
| 2,971,851 | 2/1961 | Kurtz | 195/99 |
| 3,224,946 | 12/1965 | Raymond | 195/116 |

*Primary Examiner*—Alvin E. Tanenholtz
*Attorney, Agent, or Firm*—Beveridge, DeGrandi, Kline & Lunsford

[57] ABSTRACT

An enzymatic substrate adsorbed on a solid carrier with a large specific surface area of over 50 m$^2$/g. The enzymatic substrate shall be stable in the absence of the corresponding enzyme and essentially non-soluble in water. The substrate containing layer surrounding the carrier may also comprise diluents and thickeners. The substrate-carrier together with an enzyme and a pH indicating substance is also useful as a time-temperature indicating device.

18 Claims, No Drawings

ENZYMATIC SUBSTRATE COMPOSITION ADSORBED ON A CARRIER

This application is a continuation of application Ser. No. 783,509, filed Mar. 31, 1977, which in turn is a continuation of application Ser. No. 489,667, filed July 18, 1974, now U.S. Pat. No. 4,043,871, issued Aug. 23, 1977, which in turn is a continuation-in-part of application Ser. No. 354,412, filed Apr. 25, 1973, now abandoned.

This invention relates to a substrate for enzymes, more particularly to a substrate of this kind which is applied and fixedly bound to a carrier.

Definitionwise, in the context of this application, a substrate is a substance acted upon by an enzyme or ferment.

In most enzymatic reactions, i.e. reactions in which a substrate by the catalytic action of an enzyme undergoes a modification (usually degradation) both the substrate and the enzyme are in the form of a solution and in some cases a suspension. Several advantages, not the least with regard to transportation and handling, would be gained if either of the components, i.e. the enzyme or the substrate, could be supplied on a carrier. It is known to combine an enzyme with a carrier, such as gel or cellulose.

It is also known to combine a substrate with a carrier, but the prior art combination has been performed in such a way that the substrate via a coupler was bound covalently to the carrier, or the substrate has been applied only loosely to a carrier so that it can readily be removed therefrom, for instance by the action of water. As an example of the prior art technique mention may be made of the article "Trägergebundene biologisch aktive Substanzen und ihre Anwendung" by H.D. Orth and W. Brummer in Angewandte Chemie, volume 84 (1972), No. 8, pp 319–368. This article primarily relates to enzymes adsorbed on carriers, but in Table 1 cites several references which deal with substrates adsorbed on carriers. Common to all these references is that they relate to substrates which are chemically bound to a carrier, i.e. by covalent bond or ionic bond (anionic). The intention is to exploit the substrates adsorbed on carriers for the preparation, in a pure condition, of enzymes. In this case there only occurs an enzyme-substrate complex formation without any degradation of the substrate. U.S. Pat. No. 2,677,917 and French Pat. No. 2,071,058 further disclose as known the application to carriers, such as charcoal or expanded perlite, of nutrient media for spawns of fungi. The nutrient media utilized are water soluble and permit the spawns of fungi to absorb the nutrient in a moist medium for supporting growth. A corresponding disclosure is made in U.S. Pat. No. 3,251,749 for bacterial conversion into polysaccharides of carbohydrates which are disposed on carriers. In this case also, the "substrate" is water soluble and but loosely placed on the carrier.

As further examples of the prior art technique mention may be made of French Pat. No. 1,306,640 which describes the embedding of enzymes or enzymatic substrates in apermeable material, such as polymer material. French Pat. No. 595,782 describes the application of sulphuric acid to kieselguhr. British Pat. Specification No. 891,467 describes the application of an active substance capable of oxidizing or reducing action (quinone-hydroquinone), to various carriers. U.S. Pat. No. 2,717,852 describes the application of enzymes to carriers. French Pat. No. 940,108 relates to reinforcing fillers for rubber, which fillers consist of fine-grained mineral material coated with a surface active or lubricating agent, such as oil or fat. U.S. Pat. No. 1,979,380 describes the coating of pigment particles, such as carbon black, with organic matter, such as linseed oil. British Pat. Specification No. 993,944 describes the coating of sodium aluminium silicate of large surface area with a dye. U.S. Pat. No. 2,354,318 describes the coating of fine-grained calcium carbonate with an adhesive, the product being intended as pigment for instance in wallpapers.

Contrary to what has thus been proved to be prior art, the present invention relates to a specific type of substrates adsorbed on carriers, the substrate not being covalently bound to the carrier either directly or via couplers, but being fixedly bound to the carrier by adsorption owing to interaction between the substrate and a special carrier of large specific surface area. It is further a prerequisite of the invention that the substrate has a low solubility in water and does not undergo hydrolysis or dissolution in the absence of the corresponding enzyme. Contrary to some of the above-mentioned patent specifications, in which the coating is a loosely applied, water soluble material, the substrate in the matter of the present invention is thus fixedly adsorbed on the carrier and besides difficultly soluble in water. By this means, the invention provides in a very simple and inexpensive manner an enzymatic substrate fixedly bound to a carrier. For the actuation of the substrate adsorbed on a carrier use is made of an enzyme in aqueous phase, and owing to the nature and the properties of the substrate adsorbed on a carrier there is obtained a high and controllable affinity between the enzyme and the substrate.

The invention thus provides a composition, adsorbed on a carrier, of enzymatic substrate, said composition comprising (1) a solid carrier inert to the enzymatic substrate and having a specific surface area of at least 50 $m^2/g$, and (2) a layer fixedly bound to the carrier by adsorption and incorporating a substrate which is difficultly soluble in water and is substantially stable in the absence of the corresponding enzyme.

In an embodiment of the invention the layer besides contains a diluent miscible with the substrate.

The diluent is preferably selected from the group of mineral oils having several hydrocarbons, higher aliphatic alcohols, ketones or ethers and polyglycols.

In another embodiment of the invention the layer can besides contain a viscosity-modifying agent.

The viscosity-modifying agent may be metal soaps, e.g. aluminium stearate.

In a further preferred embodiment of the invention the carrier has a specific surface area of at least 200 $m^2/g$.

The carrier is preferably selected from the group of organic/inorganic polymers, inorganic oxides, acids and salts.

It is specifically preferred to select the carrier from the group of aluminia, calcium carbonate, magnesium carbonate, silica aerogel and calcium phosphate.

In a special embodiment of the invention the substrate is glycerine tricapronate.

A special aspect of the invention relates to an enzymatic indicator which comprises a composition, adsorbed on a carrier, of enzymatic substrate in combination with an enzyme corresponding to the substrate, and an indicator for indicating the reaction product forming at the enzymatic reaction.

The solid bond (adsorption) which exists between the substrate and the carrier in accordance with the present invention is realized by the use of a special carrier which - as mentioned above - is solid and inert to the enzymatic substrate and which has a specific surface area of at least 50 m²/g, preferably at least 200 m²/g. Due to the solid bond obtained, any undesired separation of the substrate from the carrier is eliminated. Although it has not been fully established, the markedly increased affinity occurring between the substrate adsorbed on a carrier and the corresponding enzyme would seem to be attributable to the combination with the special carrier and primarily the large specific surface area thereof. In applying the invention, it has been found that at an increase of specific surface area of the carrier there is obtained an increasing activity or rate of reaction between the substrate and the enzyme. Thus, an increase of activity of up to ten times the normal one has been obtained.

Without any comprehensive enumeration of all of the known substrates which correspond to various enzymes, it will be realized that the invention is applicable to any substrate that satisfies the above-mentioned requirements, i.e. the substrate shall be difficultly soluble or substantially insoluble in water, by which is meant that the substrate shall have a solubility of less than 0.1% by weight in water at 20° C., and the substrate shall further be stable and not undergo hydrolysis or dissolution in the absence of the corresponding enzyme. Preferred substrates in the matter of the present invention are those which are selected from the group of glycerine tricapronate (tricaproin), tripelargonin, tributyrin and bis-3,5,5-trimethyl-hexyl adipate, mixed esters of polyvalent alcohols and organic and inorganic acids.

The carrier material specifically preferred at present is silicate in the form of aerogel having a specific surface area of about 200–300 m²/g. Such a silica aerogel is commercially available under the designation "aerosil", "Cab-O-Sil", Kiselgel G" from the firm Merck and "Fluosil" (Nynäs Petroleum AB, Sweden).

The substrate adsorbed on a carrier according to the present invention is preferably prepared in that the substrate is applied to the carrier by impregnation, the finished product being in the form of an easily handled powder which is stable in storage and free-flowing. Thus, the carrier is suspended, under agitation, in a liquid containing substrate or substrate and substrate diluent. After this treatment the added liquid is driven off. The residue is finely divided so that particles of the desired size and size distribution are obtained.

In its simplest and most basic embodiment the invention comprises carrier materials with a layer of a substrate of the type defined in the foregoing. As already mentioned, the carrier shall be solid and chemically inert to the substrate and have a surface area per unit of weight of at least 50 m²/g.

In another embodiment of the invention the layer applied to the carrier material consists not only of substrate but of substrate in combination with a diluent. In the layer located on the carrier material the substrate will thus be present, dissolved in the diluent. Contrary to the embodiment earlier described, where the entire substrate is directly accessible to the action of the enzyme, substantially only the substrate material present in the outermost part of the layer is directly accessible to the action of the enzyme in this latter embodiment.

The properties of the diluent, such as its capability of dissolving substrates, its activating or inhibiting enzyme effects, its viscosity and tendency to separate under the action of low temperatures, influences the accessibility of the substrate to the action of the enzyme. Suitable diluents are mineral oils, higher aliphatic alcohols, such as decanol, dodecanol, stearyl alcohol and polyglycols and other low volatile hydrocarbon compounds which are miscible with the substrate.

The accessibility of the substrate to the action of enzyme can be further influenced by admixture of viscosity-modifying agents, such as aluminum stearate, to the diluent.

The substrate composition according to the present invention is useful for any suitable purpose for reaction under the influence of the pertaining enzyme. It is particularly advantageous to use this carrier-adsorbed substrate of the invention at the standardisation and characterisation of enzymes. A special field of technics in which the present invention has proved to be particularly useful, is that of indicators for time-temperature responsive indication, for instance with regard to foodstuffs including also refrigerated and deep-frozen foodstuffs. Such indicators are known above all from U.S. Pat. No. 2,671,028.

Thus, if an indicator comprising an enzyme and its substrate as well as an indicating substance for indicating the reaction product forming at the enzymatic reaction, is subjected to the same conditions of storage as a foodstuff, it is possible by suitable calibration of the indicator to decide from the colour change of the indicator the storage status of the foodstuff.

A corresponding enzymatic indicator which makes use of the carrier-adsorbed substrate of the invention, comprises as active components said substrate combined with an enzyme adapted to the substrate, and an indicating substance, for instance a pH indicator, for indicating reaction products forming at the enzymatic reaction.

With the use of the substrate-carrier according to the invention and the corresponding enzyme in aqueous suspensions, there may be added to the suspension thickeners, such as water soluble, high molecular weight compounds, for instance agar or carboxy cellulose. This will give an advantage in that the thickener, for instance agar, provides a certain change of the reaction rate.

For further elucidation, the invention will be more fully described hereinbelow with reference to Examples. It should be observed, however, that these Examples are only illustrative and not restrictive. It should further be observed that apart from the enzymatic systems exemplified, of course many other enzymatic systems are useful and comprised within the spirit and scope of the present invention.

EXAMPLE 1

Preparation of a substrate-coated carrier.

100 g of fine-grained silica ("Fluosil" ® from Nynäs Petroleum, Sweden) were introduced in small portions and under agitation into 2500 ml of methylene chloride until a homogeneous suspension was obtained.

The suspension was then mixed with 100 g of glycerine tricapronate (tricaproin, TC) and agitation was continued for one further hour at room temperature.

Then the methylene chloride was removed by blowing air through filter nozzles and slight heating to 30° C. When the volume of the mixture had been reduced to 1500 ml the heating was interrupted to avoid bumping, and the continued expulsion of the methylene chloride was effected by air blowing only under continuous agitation.

Final expulsion of the methylene chloride was carried out in a warming cabinet at 50° C. After finished drying in the warming cabinet a white brittle mass was obtained, which was crushed in a mortar and screened through a sieve of desired mesh width whereby a fine-grained powder was obtained. The corresponding result was obtained when the dried white brittle mass was suspended in water and ground in a colloid mill.

EXAMPLE 2

Preparation of a carrier coated with substrate and diluent.

Fine-grained silica was suspended in methylene chloride in the same way as in Example 1. A mixture of 50 g of tricaproin and 50 g of spindle oil was added to the suspension under agitation, and agitation was continued for 1 h at room temperature.

In a manner corresponding to that in Example 1 the solvent was then removed and the resulting mass was crushed in a mortar and colloid mill, respectively. A fine-grained powder of carrier coated with substrate and diluent was obtained.

EXAMPLE 3

Example 2 was repeated with the difference, however, that aluminium stearate in an amount of 10% was added to the spindle oil. A result corresponding to that in Example 2 was obtained.

EXAMPLE 4

Example 2 was repeated but stearyl alcohol was substituted for the spindle oil. This required heating in order that the mixture of tricaproin and stearyl alcohol would be homogeneous. Otherwise the same procedure was used as in Example 2 and a corresponding result was obtained.

EXAMPLE 5

Tests were made with the substrate-coated carriers prepared according to Examples 1–3. In these tests the time-temperature-responsive indicating properties were determined upon indication in combination with the enzyme pancreas lipase. The acid forming at the enzymatic reaction was indicated by means of a pH indicator. The weight ratio of carrier to substrate-containing layer on said carrier in all of the cases was 1:1. The results are shown in Table 1 where the following abbreviations are used:

Fluosil=F; tricaproin=TC; spindle oil=S; aluminium stearate=Alst.

Table 1

| Temp. (°C.) | Relative time of change | | |
|---|---|---|---|
| | TC/F | TC/S/F | TC/S/10%Alst/F |
| +20 | 1.0 | 1.0 | 1.0 |
| +4 | 2.4 | 2.0 | 1.7 |
| −5 | 15.5 | 20.0 | 33 |
| −10 | 40.0 | 108 | 417 |
| −15 | 321 | 856 | 970 |
| −20 | 1396 | — | — |

The results of the tests confirm what has earlier been stated, viz. that starting from a certain time-temperature responsiveness of a carrier coated only with substrate this responsiveness will increase when the substrate is combined with a diluent, i.e. the relative times of change are extended. The responsiveness further increases if viscosity increasing agents, such as aluminium stearate, are added to the combination of substrate and diluent.

EXAMPLE 6

To study the action of thickeners in the aqueous suspension of enzyme-substrate 0.25% agar was added to aqueous suspensions of enzyme (pancreas lipase) and substrate-coated carrier according to Example 1. The indicating times obtained were noted and are shown as relative times of change in Table 2.

Table 2

| Temp. (°C.) | Relative time of change | |
|---|---|---|
| | TC/F | TC/F |
| | 0.25% agar | — |
| +20 | 1.0 | 1.0 |
| +4 | 2.4 | 2.4 |
| −5 | 12.7 | 15.5 |
| −10 | 84.2 | 40.0 |
| −15 | 1336 | 321 |
| −20 | >16000 | 1396 |

At the test one could clearly notice the effect of the agar at temperatures below −10° C.

EXAMPLE 7

Tests were made in order to compare the activity at the action of enzyme (pancreas lipase) on substrate (tricaproin), on the one hand, without a carrier and, on the other hand, coated on a carrier in accordance with Example 1. In the test, varying concentrations of enzyme were used and as a measure of activity the reaction product formed at 20° C. was indicated by means of a pH indicator. The results appear from Table 3.

Table 3

| Lipase concentration (μg/ml) | Time of change in minutes | |
|---|---|---|
| | TC | TC/F |
| 3 | 7.5 | <1 |
| 1 | 15 | 1.3 |
| 0.3 | 37 | 4.5 |
| 0.1 | 140 | 11.5 |
| 0.03 | 380 | 32 |

It will appear from Table 3 that the combination of substrate and carrier of large specific surface area implies an approximately tenfold increase in activity compared to the activity with substrate alone.

EXAMPLE 8

Same as in Example 7 tests were made to compare the activity at the action of enzyme on substrate, on one hand, without any carrier and, on the other hand, coated on a carrier. As enzyme use was made of pancreas lipase, the substrate was tripelargonin (TP), and the carrier was "Fluosil" V 300 which had a specific surface area of about 300 m²/g. As a measure of the activity the reaction product forming at 20° C. was indicated. The results are indicated in Table 4.

Table 4

| Relative enzyme concentration | Time of change in hours (h) | |
|---|---|---|
| | TP | TP/F |
| 32 | 21 | 4.25 |
| 16 | 28 | 12 |
| 8 | 77 | 25 |
| 4 | 240 | 46 |
| 2 | 524 | 100 |
| 1 | — | 240 |

EXAMPLE 9

Example 8 was repeated with the difference, however, that tripropionin (TPP) was used as substrate instead of tripelargonin. The enzyme was pancreas lipase and the carrier "Fluosil". The results are indicated in Table 5.

Table 5

| Relative enzyme concentration | Time of change in hours (h) | |
|---|---|---|
| | TPP | TPP/F |
| 32 | 1.25 | 0.5 |
| 16 | 4.75 | 1.25 |
| 8 | 21 | 2.5 |
| 4 | 28 | <21 |
| 2 | 70 | 21 |
| 1 | 142 | 25 |

EXAMPLE 10

Example 8 was repeated with the difference, however, that bis-3,5,5-trimethyl-hexyladipate (THA) was used as a substrate instead of tripelargonin. As before, the enzyme was pancreas lipase and the carrier "Fluosil". The results are indicated in Table 6.

Table 6

| Relative enzyme concentration | Time of change in hours (h) | |
|---|---|---|
| | THA | THA/F |
| 16 | 70 | 21 |
| 8 | 384 | 35 |
| 4 | — | 71 |
| 2 | — | 192 |
| 1 | — | 240–284 |

It appears from Examples 8–10 that the combination of substrate and carrier of large specific surface area implies a heavy increase of the activity compared to the activity with the use of a substrate without any carrier.

EXAMPLE 11

Substantially the same procedure was applied as in Example 7 with the difference, however, that "Kiselgel G" from the firm Merck was substituted as a carrier for "Fluosil". This carrier was of the following composition: 13% $CaSO_4$, 0.02% chloride, 0.03% Fe and the balance $SiO_2$. The carrier grains had a diameter of 5–25 μm. For the substrate not adsorbed on a carrier use was made of a 1% solution of tricaproin in acetone, whereas for the substrate adsorbed on a carrier use was made of a suspension containing a corresponding amount of Kiselgel coated with 30% tricaproin. After admixture of enzyme (pancreas lipase) a pH of 5.4 was determined at 20° C. after 28 minutes for the substrate adsorbed on a carrier and after 220 minutes for the substrate not adsorbed on a carrier.

It will thus be realized that by choosing suitable combinations of substrate, substrate-diluent, substrate-diluent-viscosity-modifying agent, indicators can be provided for time-temperature-responsive indication, said indicators being adapted to the conditions applicable to the storage of a certain article. It will also be realized that by reason of the very handy configuration of the substrate according to the invention the indicator may be further adapted by mixing substrate materials of different kinds, i.e. mixing a material which is coated only with substrate and a material which is coated with a combination of substrate-diluent-viscosity-modifying agent, etc. There are unthought-of avenues open for an adaptation or control of the time-temperature responsiveness of the indicator, and by making use of the substrate according to the invention indicators can be provided which are adapted to every conceivable purpose, be it for the indication of photographic material, medicines, foodstuffs or other sensitive articles which for their keeping qualities require certain definite storage conditions.

It should be observed that the above specification is merely meant to be informative but not restrictive. Obviously, many modifications and variations may be resorted to within the spirit and scope of the invention such as it is defined in the appended claims.

What we claim and desire to secure by Letters Patent is:

1. A composition capable of undergoing enzymatic reaction and of indicating formation of reaction product formed by said enzymatic reaction, said composition comprising:
   (a) a suspension of a carrier-substrate combination comprising:
      (1) a solid granular carrier with a specific surface area of at least 50 $m^2/g$; and
      (2) a substrate-containing layer in which said substrate is an enzymatic substrate capable of undergoing an enzymatic reaction, said layer derived by impregnation of the carrier with a non-aqueous substrate solution and removing the solvent, said layer being fixedly bound to said carrier by adsorption; said substrate having a solubility of less than 0.1% by weight in water at 20° C. and being stable and free from hydrolysis and dissolution in the absence of its specific enzyme; said carrier being inert to said substrate;
   (b) an enzyme for said enzymatic substrate; and
   (c) an indicator for indicating said reaction product formed when said enzyme reacts with said enzymatic substrate.

2. A composition in accordance with claim 1 wherein said carrier is silica aerogel with a specific surface area of at least 200 $m^2/g$; and fixedly bound to said carrier by adsorption is a layer of glycerine tricapronate, which functions as a substrate for the enzyme lipase.

3. A composition in accordance with claim 1 wherein said carrier is silica aerogel with a specific surface area of at least 200 $m^2/g$; and fixedly bound to said carrier by adsorption is a layer consisting of glycerine tricapronate, which functions as a substrate for the enzyme lipase and spindle oil.

4. A composition according to claim 1 wherein said indicator is a pH indicator.

5. A composition in accordance with claim 4, wherein the substrate-containing layer further comprises a diluent selected from the group consisting of mineral oils, higher aliphatic alcohols, ketones, ethers, and polyglycols.

6. A composition in accordance with claim 4, wherein the substrate-containing layer further comprises a viscosity-modifying agent.

7. A composition in accordance with claim 6, wherein the viscosity-modifying agent is aluminum stearate.

8. A composition in accordance with claim 4, wherein the carrier is selected from the group consisting of organic polymers, inorganic polymers, inorganic oxides, acids and salts.

9. A composition in accordance with claim 8, wherein the carrier is selected from the group consisting of alumina, calcium carbonate, magnesium carbonate, silica aerogel and calcium phosphate.

10. A composition in accordance with claim 4, wherein the carrier has a specific surface area of at least 200 $m^2/g$.

11. A composition in accordance with claim 4, wherein the substrate is selected from the group consisting of glycerine tricapronate, tripelargonin, tributyrin, bis-3,5,5-trimethyl hexyl adipate, mixed esters of polyvalent alcohols and organic and inorganic acids.

12. A composition in accordance with claim 4 wherein said carrier is silica aerogel with a specific surface area of at least 200 $m^2/g$; and fixedly bound to said carrier by adsorption is a layer of glycerine tricapronate, which functions as a substrate for the enzyme lipase.

13. A composition in accordance with claim 4 wherein said carrier is silica aerogel with a specific surface area of at least 200 $m^2/g$; and fixedly bound to said carrier by adsorption is a layer consisting of glycerine tricapronate, which functions as a substrate for the enzyme lipase and spindle oil.

14. A composition in accordance with claim 4, wherein the viscosity-modifying agent is aluminum stearate.

15. A composition in accordance with claim 4, wherein the carrier is selected from the group consisting of alumina, calcium carbonate, magnesium carbonate, silica aerogel and calcium phosphate.

16. An improved method for standardizing an enzyme be reacting said enzyme with an enzymatic substrate for said enzyme and measuring the concentration of reaction product formed to determine the activity of said enzyme, wherein the improvement comprises:
 (a) providing a composition according to claim 1,
 (b) reacting said enzyme with said enzymatic substrate.

17. A method of using a carrier-substrate combination in enzymatic reaction, said method comprising:
 (a) providing a composition according to claim 1, and
 (b) reacting said enzyme with said enzymatic substrate.

18. A method of using a carrier-substrate combination in enzymatic reaction, said method comprising:
 (a) providing a composition according to claim 4, and
 (b) reacting said enzyme with said enzymatic substrate.

* * * * *